(12) United States Patent
Aulbach (10) Patent No.: US 7,852,990 B2
(45) Date of Patent: Dec. 14, 2010

(54) BEAM ADMISSION UNIT, BEAM GENERATION DEVICE AND TOMOGRAPHY DEVICE

(75) Inventor: Peter Aulbach, Forchheim-Kersbach (DE)

(73) Assignee: Siemens Aktiengesellschaft, Munich (DE)

(*) Notice: Subject to any disclaimer, the term of this patent is extended or adjusted under 35 U.S.C. 154(b) by 53 days.

(21) Appl. No.: 12/292,923

(22) Filed: Dec. 1, 2008

(65) Prior Publication Data

US 2009/0141858 A1    Jun. 4, 2009

(30) Foreign Application Priority Data

Dec. 3, 2007    (DE) .................... 10 2007 058 104

(51) Int. Cl.
*G21K 1/02* (2006.01)

(52) U.S. Cl. .................... 378/148; 378/149

(58) Field of Classification Search .......... 378/147–149
See application file for complete search history.

(56) References Cited

U.S. PATENT DOCUMENTS

| | | | | |
|---|---|---|---|---|
| 2,814,727 A | * | 11/1957 | Konrad Gund et al. | 250/396 R |
| 4,172,979 A | * | 10/1979 | Morrison | 378/65 |
| 4,203,037 A | * | 5/1980 | Gur et al. | 378/37 |
| 4,277,685 A | * | 7/1981 | Covic et al. | 378/7 |
| 4,679,221 A | * | 7/1987 | O'Brien et al. | 378/148 |
| 4,788,699 A | * | 11/1988 | Dobert et al. | 378/38 |
| 4,998,270 A | * | 3/1991 | Scheid et al. | 378/155 |
| 5,233,193 A | * | 8/1993 | Arakawa | 250/580 |
| 5,596,618 A | * | 1/1997 | Ogushi | 378/34 |
| 6,396,902 B2 | * | 5/2002 | Tybinkowski et al. | 378/150 |
| 6,788,764 B2 | * | 9/2004 | Saladin et al. | 378/152 |
| 7,092,490 B2 | * | 8/2006 | Saladin et al. | 378/156 |
| 7,236,572 B2 | * | 6/2007 | Maschke | 378/146 |
| 7,317,786 B2 | * | 1/2008 | Distler et al. | 378/150 |
| 7,386,097 B2 | * | 6/2008 | Kerpershoek et al. | 378/149 |

FOREIGN PATENT DOCUMENTS

| | | |
|---|---|---|
| DE | 578 443 | 5/1933 |
| DE | 578443 C | 6/1933 |
| DE | 3138730 A1 | 4/1983 |

* cited by examiner

*Primary Examiner*—Edward J Glick
*Assistant Examiner*—Thomas R Artman
(74) *Attorney, Agent, or Firm*—Harness, Dickey & Pierce, P.L.C.

(57) ABSTRACT

A beam admission unit is disclosed. In at least one embodiment, the beam admission unit includes a plurality of admission segments having at least one admission slit for admitting radiation emanating from a radiation source onto a predetermined admission region. So as to implement a particularly space-saving, robust and reliable design, in at least one embodiment the admission segments are interconnected in an articulated fashion to form an admission plate chain which can be rolled up.

33 Claims, 4 Drawing Sheets

BEAM ADMISSION UNIT, BEAM GENERATION DEVICE AND TOMOGRAPHY DEVICE

PRIORITY STATEMENT

The present application hereby claims priority under 35 U.S.C. §119 on German patent application number DE 10 2007 058 104.3 filed Dec. 3, 2007, the entire contents of which is hereby incorporated herein by reference.

FIELD

Embodiments of the invention generally relate to a beam admission unit, a beam generation device and/or a tomography device having a beam admission unit.

BACKGROUND

Beam admission devices are used, for example, in x-ray machines such as x-ray computed tomography devices for admitting the x-ray radiation emanating from an x-ray source onto a desired examination or detection region, for example in the form of a fan. By way of the admission unit, inter alia, direct irradiation outside of the desired examination region by the x-ray radiation can be avoided, at least to the greatest extent. The latter in particular decreases the radiation dose applied during the examination of a body.

It is known to use a slit screen to admit the x-ray radiation; the former comprises a planar tantalum plate with admission slits provided therein. By using admission slits having different widths, it is possible to admit the x-ray radiation emanating from an x-ray source onto examination or detection regions having different widths, which is desirable in the case of x-ray computed tomography using multirow detectors, for example. It is possible to obtain different admissions by longitudinal displacement of the tantalum plate, that is to say a displacement perpendicular to the longitudinal direction of the admission slits, which positions a respectively suitable admission slit on the beam port of the x-ray source.

However, it is disadvantageous in this case that the length of the tantalum plate rapidly increases with an increasing number of desired admission regions and hence increasing number of admission slits. Occasionally, this is due to the fact that, depending on the geometric conditions, a prescribed minimum distance has to be observed between adjacent admission slits. The minimum distance depends on, inter alia, the distance of the tantalum plate from the beam port and the aperture of the beam port. The space available for attaching and to-and-fro displacement of the tantalum plate is substantially limited by housing walls and the like, for example by the housing of the gantry of an x-ray computed tomography scanner, which should be as thin as possible for patient-psychological reasons; hence the number of admission possibilities that can be implemented is limited.

In addition, the complexity involved for the mechanical support of the tantalum plate increases with increasing linear dimensions. This is all the more important in x-ray computed tomography since non-negligible acceleration forces act on the tantalum plate during circular or helical scans of the body.

Furthermore, conventional drive systems for moving the tantalum plate to-and-fro, which for example comprise a motor-driven threaded spindle for moving the tantalum plate, have a low dynamic range. The latter means that, for example, setting two admission possibilities based on two admission slits which are at a distance from one another requires a relatively long time; this is in contrast to a time-optimized examination of a body, in particular using different recording modes. In addition, a drive system with a threaded spindle is not very stiff and has relatively high wear and tear. However, high wear and tear in turn leads to the play in the drive unit rapidly increasing, which reduces in a non-negligible way the achievable positional accuracy of the admission slits.

It is known to design the tantalum plate in an arced shape, in particular in order to decrease its linear extent. However, in this case too, the space available in the cramped spatial conditions is quickly exhausted with increasing numbers of admission slits, in particular with respect to the minimum distance of the admission slits.

For example, so-called jaw screens provide a space-saving implementation of a multiplicity of admission possibilities. These screens can for example comprise two jaws which can be moved against one another, or two eccentrically mounted rollers which can be rotated. Moving the jaws or rotating the rollers affords the possibility of realizing many admission slits with different widths. However, a disadvantage of the jaw screen is that two jaws or rollers always have to be synchronously moved in order to set a desired width of an admission slit. This makes the design, and the required control and drive devices for setting the admission slit, more complicated and more expensive.

SUMMARY

At least one embodiment of the invention reduces or even eliminates at least one of the disadvantages of the prior art. In particular, a beam admission unit of at least one embodiment is intended to be specified which affords the possibility of a multiplicity of admission possibilities by way of a particularly space-saving design. Furthermore, a mechanically robust beam admission unit of at least one embodiment is intended to be specified which affords the possibility of very dynamically interchanging different admission possibilities. Moreover, a beam admission unit of at least one embodiment is intended to be specified which has a compact design and which at the same time affords the possibility of examining a body using a particularly low radiation dose. It is a further goal to specify, in at least one embodiment, a beam generation device and/or a tomography device in an analogous statement of the object.

A first aspect of at least one embodiment of the invention relates to a beam admission unit with a plurality of admission segments. Each admission segment has at least one admission slit for admitting radiation emanating from a radiation source onto a predetermined admission region. In particular, the radiation can be x-ray or gamma radiation. The admission slit can be in the form of a thinning of the admission segment, or even a slit-like recess penetrating the admission segment. Deviating from this, within the scope of the invention, the admission slit can also be designed differently depending on, inter alia, the respectively desired admission width and shape, the type of radiation and the latter's energy.

The admission segments are arranged one behind the other, interconnected in an articulated fashion and form an admission plate chain in this way. The admission plate chain thus comprises a number of admission segments, interconnected by means of articulated connections. The admission segments can be moved relative to one another by means of these articulated connections, for example about respective rotational axes. This affords the possibility of, for example, rolling up or unrolling the admission segments like a roller blind, as a result of which a particularly space-saving design can be attained, even in the case of a multiplicity of admission segments, that is to say a multiplicity of admission slits and admission possibilities connected to this. In addition to the rolling up and unrolling, any number of other alternatives suitable for space-saving reception and housing of the admission plate chain are feasible, such as curved guide rails or the like. In addition to the space-saving and compact design, a particularly advantageous mechanical stability can moreover be attained. Rolling up and unrolling the admission plate chain onto one or more roller-shaped receptacles is mentioned by way of example without limiting the generality.

By rolling up and unrolling the admission plate chain, combined with corresponding guide rails, it is possible to move the admission segments past the beam port and position the respectively suitable admission segment in front of the beam port in order to set a respectively desired admission.

A second aspect of at least one embodiment of the invention relates to a beam generation device, comprising a radiation source, in particular an x-ray or gamma radiation source, for generating the respective radiation, and a beam admission unit according to the first aspect of at least one embodiment of the invention arranged downstream of the radiation source in the emission direction.

A third aspect of at least one embodiment of the invention relates to a tomography device, in particular an x-ray computed tomography device, comprising a radiation source for generating the radiation; a radiation detector arranged opposite the radiation source in the emission direction of the radiation; and a beam admission unit arranged downstream of the radiation source in the emission direction according to the first aspect of at least one embodiment of the invention. Advantages and advantageous effects of the second and third aspect of at least one embodiment of the invention emerge from the advantages and advantageous effects according to the first aspect of at least one embodiment of the invention.

BRIEF DESCRIPTION OF THE DRAWINGS

In the following text, example embodiments of the invention, and in particular further advantages and advantageous effects, will be explained in more detail with reference to the figures, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected, " or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, identical, or functionally identical, elements are referred to throughout using the same reference symbols. The illustrations in the figures are schematic and not necessarily true to scale, with the scales possibly varying between the figures. In the following text, the x-ray computed tomography device and the beam generation device are—without limiting the generality—only discussed to the extent considered to be necessary for understanding the invention.

Figure 1:
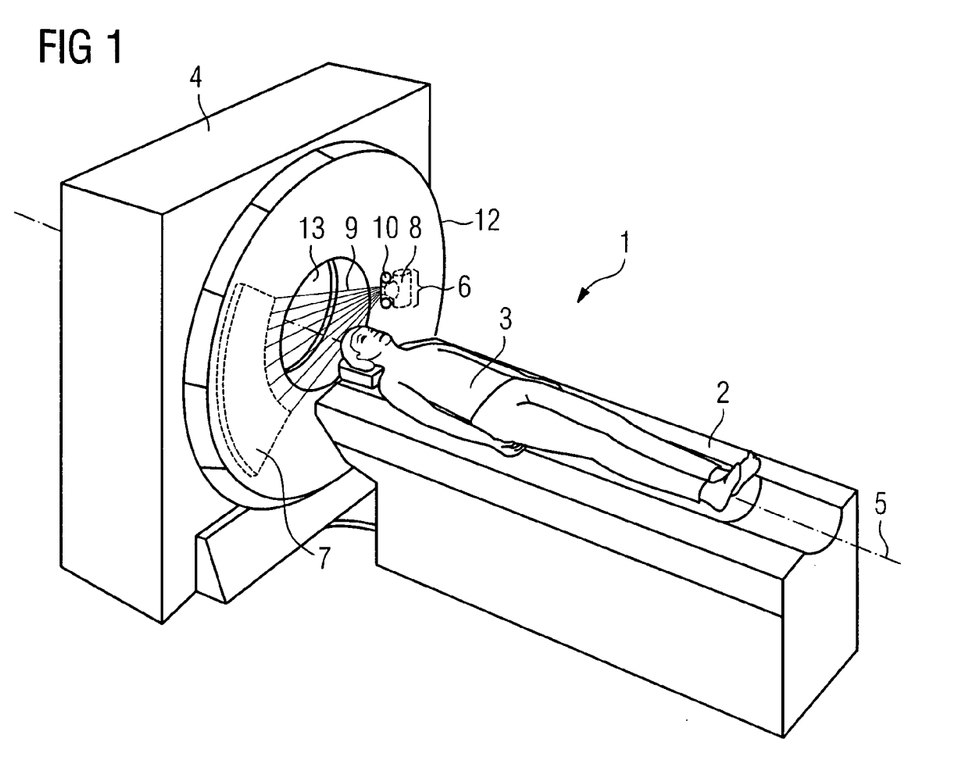
FIG. 1 shows an x-ray computed tomography device according to the third aspect of an embodiment of the invention.

FIG. 1 schematically shows an x-ray computed tomography device 1, as an example of a tomography device, according to the third aspect of an embodiment of the invention. The x-ray computed tomography device 1 has a patient couch 2 on which a patient 3 to be examined (also referred to as a body in the following text) is positioned. Provision is made in a gantry 4 for a beam generation device 6 and, arranged opposite it, a detector 7 such that they can rotate about a system axis 5. The beam generation device 6 comprises an x-ray tube 8 for generating x-ray radiation 9. A beam admission unit 10 is arranged downstream of the x-ray tube 8 in the emission direction of the x-ray radiation 9, that is to say in the direction of the detector 7 starting from the x-ray tube 8.

In order to examine the body 3 or an area of interest of the latter, it is scanned, e.g. circularly or helically, by the x-ray radiation 9 emanating from the beam generation device 6. In the process, the x-ray radiation 9 passes through the body 3 and is attenuated when passing through the body 3 in accordance with the respective absorption properties of the body 3. The part of the x-ray radiation 9 transmitted through the body 3 is detected by means of the detector 7. A, for example, two- or three-dimensional display of at least the part of the body 3 of interest can be determined based on the measurement data of the detector 7 which reflects the absorption properties of the body 3.

The detector 7 is—without limiting the generality—a multirow, pixelated detector. It has a number of detector rows 11, parallel to the system axis 5, which are only shown in FIG. 4. The number of detector rows 11 can differ from the illustration in FIG. 4. Furthermore, within the scope of at least one embodiment of the invention, provision can also be made for detector rows 11 of varying width so that different layers of the body 3 can be scanned.

Additionally, housing walls and a gantry opening, through which the body 3 can be moved during an examination, are referred to by reference symbols 12 and 13. Reference is already made here to the fact that the space available for mounting and operating the beam admission unit 10 is significantly limited by the housing walls 12 and the width B of the gantry opening 13 in the direction of the system axis 5 which is occasionally restricted by non-technical, patient-specific circumstances.

Figure 2:
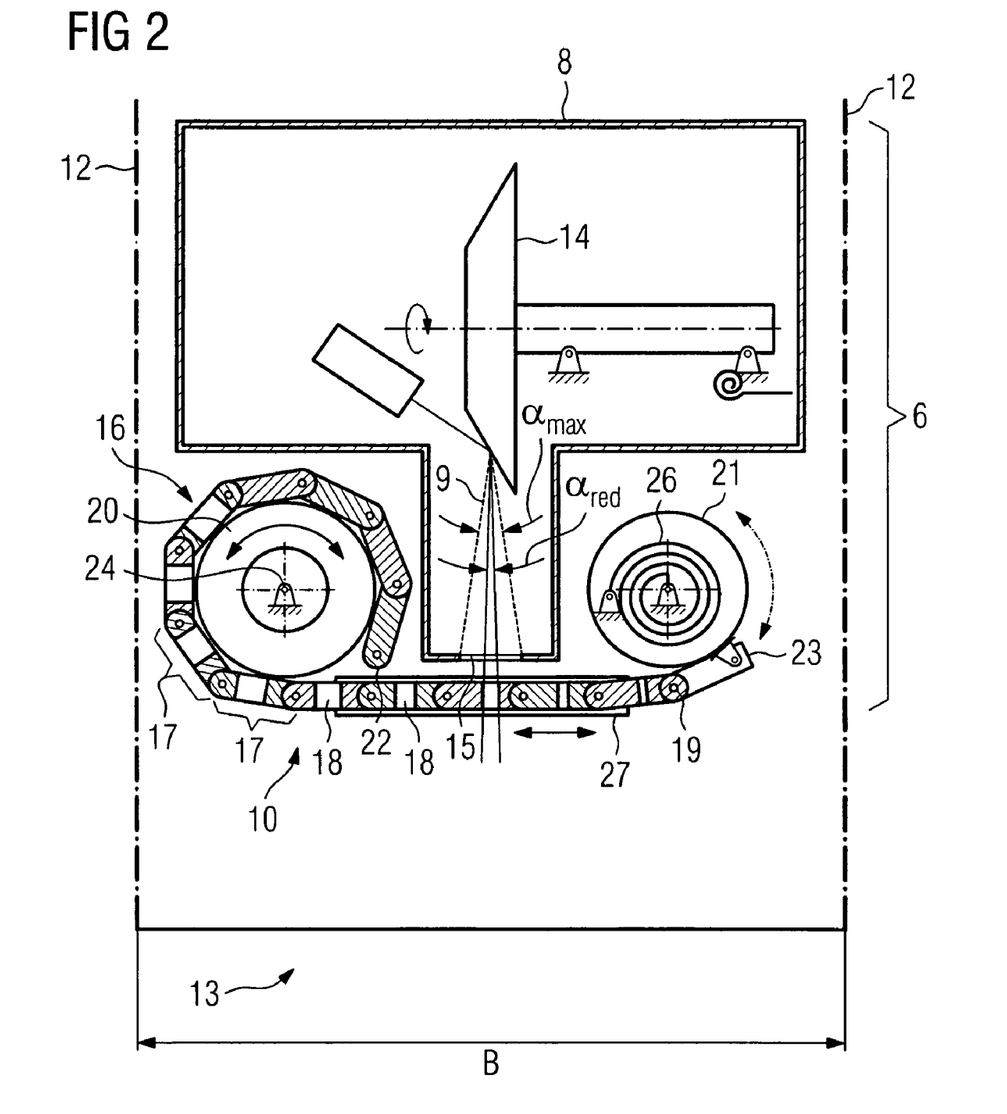
FIG. 2 shows a cross-sectional illustration of a beam generation device according to the second aspect of an embodiment of the invention, comprising an x-ray tube and a beam admission unit according to the first aspect of an embodiment of the invention.

FIG. 2 shows a cross-sectional illustration of the beam generation device 6 in a plane perpendicular to the system axis 5, with the beam generation device 6 comprising the x-ray tube 8 and the beam admission unit 10, as already mentioned above. The housing walls 12 of the gantry 4, located to the left and right of the beam generation device 6, are indicated by the dashed lines.

X-ray radiation is generated in a conventional fashion by means of the x-ray tube 8 by electron bombardment of an anode 14 which in the present case has an annular design. The x-ray beams, emitted in the direction of the gantry opening 13 due to the beveled shape of the anode 14, can escape the housing of the x-ray tube 8 through a beam port 15. A maximum aperture $\alpha_{max}$ for the x-ray radiation 9 is defined by the beam port 15.

In some applications or examination protocols, limiting the maximum aperture $\alpha_{max}$ is desirable or required. The later is the case, for example, if body layers having differing thicknesses are intended to be scanned.

Figure 4:
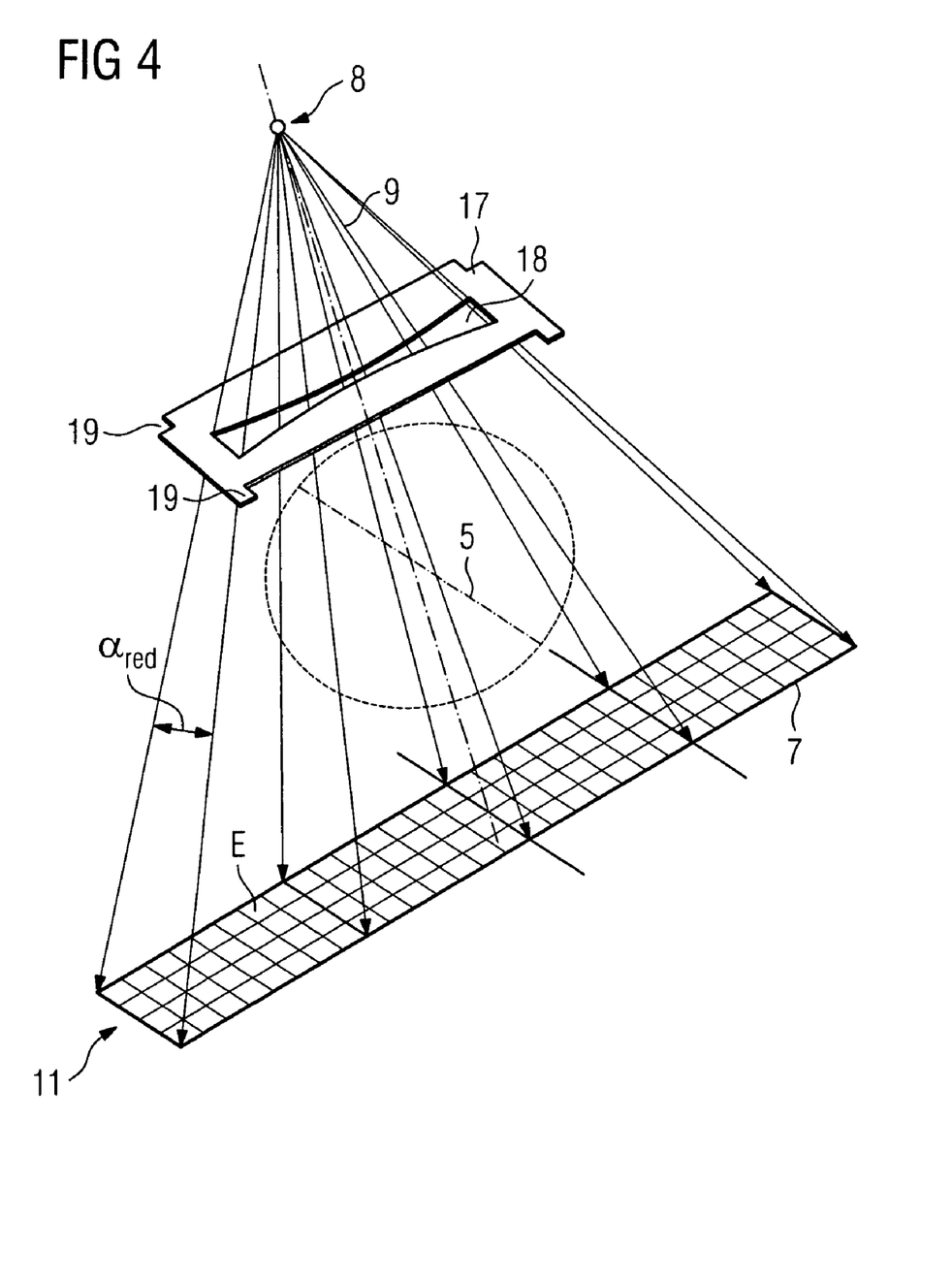
FIG. 4 shows a perspective view of a variation of an admission segment of the beam admission unit according to FIG. 3.

The beam admission unit 10 is provided for limiting the maximum aperture $\alpha_{max}$ to a respectively required reduced aperture $\alpha_{red}$, that is to say for admitting the x-ray radiation 9 onto a desired or prescribed admission region E on the detector 7 (see FIG. 4). The beam admission unit 10 comprises an admission plate chain 16, which in turn has a number of interconnected admission segments 17 connected in an articulated fashion. Each admission segment 17 has an admission slit 18 designed to admit the x-ray radiation 9.

As can be seen from FIG. 2, the admission segments 17 form individual elements of the admission plate chain 16. The admission segments 17 are arranged one behind the other, with in each case two admission segments 17 lying one behind the other, that is to say a first and a second, adjacent admission segment, being connected to one another by means of an articulated connection 19 so that they can be moved relative to one another.

The articulated connection 19 can basically be any type of articulated connection. Without limiting the generality, the following are mentioned as articulated connections 19: hinge joints, ball and socket joints. In the case of a hinge joint, a joint head, for example on the first admission segment, is generally enclosed by a joint recess, for example on the second admission segment, with a rotation of the first admission segment relative to the second admission segment about a common rotational axis 24 (FIG. 2) being possible. In the case of a ball and socket joint, the joint head and joint recess have a spherical design.

The admission segments 17 of the admission plate chain 16 can have substantially arbitrary widths in their longitudinal direction, corresponding to the respective demands on the admission of the x-ray radiation 9. In the case illustrated in FIG. 2, the admission segments 17 have the same width and can basically cover the entire width of the beam port 15. This can avoid excessive radiation in the case of a respectively set admission possibility, that is to say undesired radiation can be prevented from passing through the space between two adjacent admission segments 17 or through a neighboring admission slit 18. As can be seen from FIG. 3, the admission segments 17 are arranged one behind the other in such a way that spaces between the admission segments 17 and the first possibility of excessive radiation are avoided. By way of example, this can be achieved by means of a for example step-like overlap of two adjacent admission segments 17 and the like (not shown).

By way of an identical structural width of the admission segments 17, the admission segments 17 can be interchanged without any problem and can be arranged one behind the other in an arbitrary sequence without changing the overall length of the admission plate chain 16 and the positioning prescriptions for positioning a particular admission segment 17 at a prescribed location in the admission plate chain 16. Inter alia, this also allows simple adaptation for different detector types which have a different number of detector rows 11 and different widths of the detector rows 11. With regard to simple positioning and avoiding excessive radiation, it is also advantageous if the admission slits 18 of the admission segments 17 are arranged centrally in the longitudinal direction of the admission plate chain 16.

Figure 3:
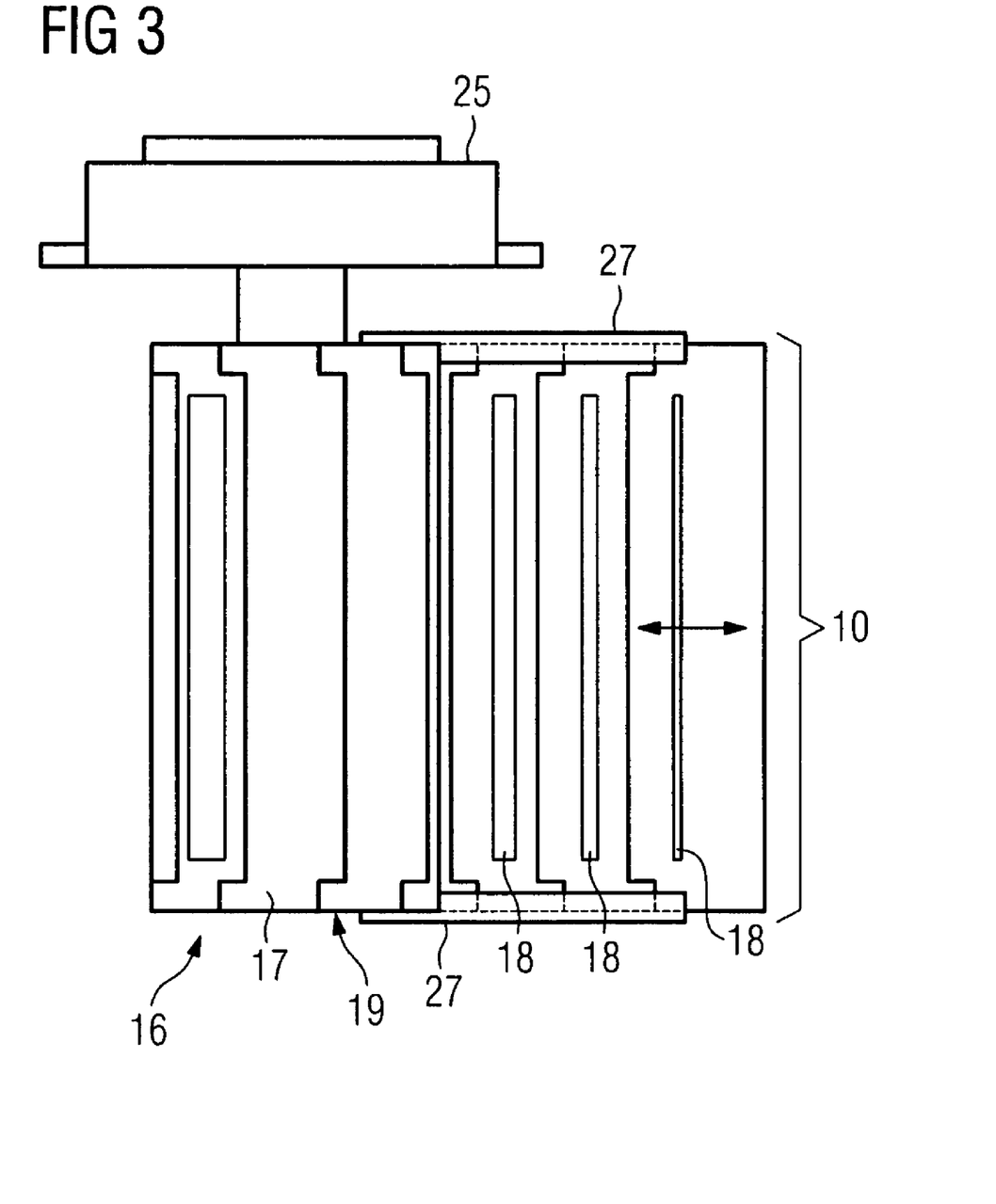
FIG. 3 shows a plan view of the beam admission unit according to FIG. 2.

As can be seen from the cross-sectional illustration in FIG. 2, the admission slits 18 have, with respect to the longitudinal direction of the admission plate chain 16, different widths in the sectional plane relevant to FIG. 2, which widths reflect the admission possibilities. The admission slits 18 can be rectangular, as can be seen in the plan view in FIG. 3. The shape of the admission slits 18 also depends on, inter alia, the respective section of the body 3 to be scanned or the respective body layer to be scanned. If the admission segments 17 are of planar design, as is illustrated in FIG. 2 and FIG. 3, it is possible that there is barrel-shaped excessive radiation on the admission region E provided on the detector 7. The latter leads to the patient 3 being unnecessarily exposed to radiation. Such excessive radiation can be avoided by suitably shaped admission slits 18. The admission slits 18 can, for example, be tapered toward their center with respect to their longitudinal direction, as is shown in FIG. 4. The tapered shape affords the possibility of only a, for example rectangular, detection region relevant for imaging being admitted onto the detector 7. This affords the possibility of requiring a particularly small amount of space and at the same time significantly reducing the exposure of the patient to radiation.

So that a large enough proportion of the x-ray radiation 9 is absorbed by the admission segments 17, these can be produced from, for example, tantalum, tungsten or another radiation absorbing material which can satisfy the respective absorption requirements. The required degree of absorption of the admission segments 17 sometimes depends on the respective application and the respectively desired degree of the reduction in the radiation dose.

As can be seen from FIG. 2 and FIG. 3, the beam admission unit 10 furthermore comprises a first cylinder roll receptacle 20 and a second cylinder roll receptacle 21. A first end 22 of the admission plate chain 16 is connected to the first cylinder roll receptacle 20, and a second end 23, at the far end from the first end 22, is connected to the second cylinder roll receptacle 21. Although the cylinder roll receptacles 20 and 21 are in the shape of a barrel, other shapes which are suitable for rolling up or unrolling the admission plate chain onto or from them are also feasible within the scope of the invention. The first 20 and second 21 cylinder roll receptacles are mounted such that they can rotate about the respective rotational axis 24. The first cylinder roll receptacle 20 is connected to a stepper motor 25 for its rotational drive. The second cylinder roll receptacle 21 is pre-stressed against the first cylinder roll receptacle 20 by means of a helical spring so that the admission plate chain 16 is acted on by a tensioning force acting between the first 20 and second 21 cylinder roll receptacles. A play of the admission plate chain 16 detrimental to a positionally-exact setting of an admission possibility can be substantially reduced by the pre-stressing.

A guide unit for guiding the admission segments 17 along a prescribed guide path in the longitudinal direction of the admission plate chain 16 is arranged between the first cylinder roll receptacle 20 and the second cylinder roll receptacle 21. In the present case, the guide path is prescribed by two (in general at least one) guide rails 27 such that the admission segments 17 can be led past, and positioned in front of, the beam port 15 in such a fashion that the respectively desired admission can be set.

The admission segments 17, connected in an articulated fashion according to the invention, can be rolled up onto or unrolled from the first 20 and second 21 cylinder roll receptacles. This affords the possibility of implementing a multiplicity of admission possibilities, basically given by the number of admission segments 17, while at the same time having a particularly space-saving embodiment of the beam admission unit 10. The number of admission possibilities that can be implemented is limited to a substantially smaller extent by the housing walls 12 (see FIG. 2) and the like compared to known, planar admission plates. Additionally, the beam admission unit 10 is robust and affords the possibility of rapid and precise displacement of the admission segments 17, for example by way of a stepper motor flange-mounted directly, or via a transmission, to the first cylinder roll receptacle 20. This means that different admission possibilities can be set quickly and very precisely. In particular, the displacement can be effected in a time window of the order of milliseconds, which is expedient for x-ray computed tomography. It is possible that in addition to the abovementioned advantages, the radiation exposure of the patient 3 to be examined can be kept particularly low by means of a suitably chosen average width of the admission slits 18. Furthermore, the beam admission unit 10 according to the invention having a multiplicity of admission possibilities can be produced with comparatively small structural complexity and at a low cost.

Deviating from the preceding illustration, it is also possible that provision is only made for one cylinder roll receptacle, and the part of the admission plate chain 16 not held therein is held in guide rails and guided in the latter. In the process, it is possible that, in a way similar to the above, the second end 23 is pre-stressed against the first cylinder roll receptacle by way of a pre-stressing unit, e.g. a helical spring. The course of the guide rails can, for example, be adapted to the spatial conditions within the gantry 4. For example, the guide rails can extend linearly in the region of the beam port 15 and have a spiral profile in an adjacent region so that the part of the admission plate chain 16 unrolled from the first cylinder roll receptacle 20 can be held in a space-saving fashion. It is also possible that the admission plate chain 16 is only guided in guide rails, without cylinder roll receptacles being provided. To this extent, the embodiments shown in the figures should not be considered to be limiting. Rather, further beam admission units, modified with respect to the figures, are feasible and possible within the scope of at least one embodiment of the invention.

It is clear, in particular from the above description and the above example embodiments, that the beam admission unit according to the invention, the beam generation device and the tomography device achieve objects on which embodiments of the invention are based. Thus, provision can be made especially for a particularly space-saving, robust and reliable beam admission unit.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A beam admission unit, comprising:
a plurality of admission segments aligned adjacent to one another to form an admission plate chain, interconnected in an articulated fashion and respectively including at least one admission slit to admit radiation emanating from a radiation source onto an admission region: wherein
the admission slits of at least two admission segments have mutually differing average admission widths.

2. A beam generation device, comprising:
a radiation source to generate radiation, the radiation source having an exit window through which the radiation exits with a maximally expanded beam cone during operation; and
a beam admission unit including a plurality of admission segments aligned adjacent to one another to form an admission plate chain, interconnected in an articulated fashion and respectively including at least one admission slit to admit radiation emanating from the radiation source onto an admission region: wherein
the beam admission unit is arranged downstream of the exit window of the radiation source in an emission direction of the radiation such that the at least one admission slit restricts the maximally expanded beam cone of radiation into a single, smaller cone of radiation.

3. The beam generation device as claimed in claim 2, wherein an articulated connection, formed between a first and a second admission segment which is adjacent to the first in the longitudinal direction of the admission plate chain, is designed as a hinge joint.

4. The beam generation device as claimed in claim 2, wherein an articulated connection, formed between a first and a second admission segment which is adjacent to the first in the longitudinal direction of the admission plate chain, is designed as a ball and socket joint.

5. The beam generation device as claimed in claim 2, wherein the admission segments have a substantially equal width in the longitudinal direction of the admission plate chain.

6. The beam generation device as claimed in claim 2, wherein the admission slits are arranged centrally in the admission segments with respect to the longitudinal direction of the admission plate chain.

7. The beam generation device as claimed in claim 2, wherein the admission slits are tapered toward their center with respect to their longitudinal direction.

8. The beam generation device as claimed in claim 2, wherein the admission segments are produced from a radiation absorbing material.

9. The beam generation device as claimed in claim 8, wherein the radiation absorbing material is tantalum or tungsten.

10. The beam generation device as claimed 2, wherein the beam admission unit further comprises:
at least one cylinder roll receptacle, mounted to rotate and connected to a first end of the admission plate chain, for rolling up or unrolling the admission plate chain.

11. The beam generation device as claimed in claim 10, wherein the beam admission unit further comprises:
a further cylinder roll receptacle, mounted to rotate and connected to a second end of the admission plate chain, for unrolling or rolling up the admission plate chain.

12. The beam generation device as claimed in claim 11, further comprising:
a guide unit to guide the admission segments in the longitudinal direction of the admission plate chain along a guide path prescribed by the guide unit.

13. The beam generation device as claimed in claim 12, wherein the guide unit includes at least one guide rail for guiding the admission segments on a guide path fixed by the guide rail between the cylinder roll receptacle and the further cylinder roll receptacle.

14. The beam generation device as claimed in claim 11, wherein at least one of the cylinder roll receptacle and the further cylinder roll receptacle includes a drive unit for rotating at least one of the cylinder roll receptacle and the further cylinder roll receptacle.

15. The beam generation device as claimed in claim 14, wherein the drive unit comprises a stepper motor to actuate at least one of the cylinder roll receptacle and the further cylinder roll receptacle directly or by way of a transmission unit.

16. The beam generation device as claimed in claim 2, wherein the at least one admission slit is useable to admit at least one of x-ray and gamma radiation.

17. The beam generation device as claimed in claim 2, wherein the radiation source is an x-ray or gamma radiation source.

18. The beam generation device of claim 2, wherein the admission slits of at least two admission segments have mutually differing average admission widths.

19. A tomography device, comprising:
a radiation source to generate radiation, the radiation source having an exit window through which the radiation exits with a maximally expanded beam cone during operation;
a radiation detector, arranged opposite the radiation source in an emission direction of the radiation; and
a beam admission unit including a plurality of admission segments aligned adjacent to one another to form an admission plate chain, interconnected in an articulated fashion and respectively including at least one admission slit to admit radiation emanating from the radiation source onto the admission region; wherein
the beam admission unit is arranged downstream of the exit window of the radiation source in an emission direction to admit the radiation onto an admission region on the radiation detector, and the at least one admission slit restricts the maximally expanded beam cone of radiation into a single, smaller cone of radiation.

20. The tomography device as claimed in claim 19, wherein the tomography device is an x-ray computed tomography device.

21. The tomography device as claimed in claim 19, wherein the radiation source is an x-ray or gamma radiation source.

22. The tomography device of claim 19, wherein an articulated connection, formed between a first and a second admission segment which is adjacent to the first in the longitudinal direction of the admission plate chain, is designed as one of a hinge joint and a ball and socket joint and.

23. The beam tomography device as claimed in claim 19, wherein the admission segments have a substantially equal width in the longitudinal direction of the admission plate chain.

24. The tomography device of claim 19, wherein the admission slits of at least two admission segments have mutually differing average admission widths.

25. The tomography device of claim 19, wherein the admission slits are arranged centrally in the admission segments with respect to the longitudinal direction of the admission plate chain.

26. The tomography device of claim 19, wherein the admission slits are tapered toward their center with respect to their longitudinal direction.

27. The tomography device of claim 19, wherein the admission segments are produced from a radiation absorbing material, in particular tantalum or tungsten.

28. The tomography device of claim 19, further comprising:

at least one cylinder roll receptacle, mounted to rotate and connected to a first end of the admission plate chain, for rolling up or unrolling the admission plate chain.

29. The tomography device of claim 28, further comprising:

a further cylinder roll receptacle, mounted to rotate and connected to a second end of the admission plate chain, for unrolling or rolling up the admission plate chain.

30. The tomography device of claim 29, further comprising:

a guide unit to guide the admission segments in the longitudinal direction of the admission plate chain along a guide path prescribed by the guide unit.

31. The tomography device of claim 30, wherein the guide unit includes at least one guide rail for guiding the admission segments on a guide path fixed by the guide rail between the cylinder roll receptacle and the further cylinder roll receptacle.

32. The tomography device of claim 29, wherein at least one of the cylinder roll receptacle and the further cylinder roll receptacle includes a drive unit for rotating at least one of the cylinder roll receptacle and the further cylinder roll receptacle.

33. The tomography device of claim 32, wherein the drive unit comprises a stepper motor to actuate at least one of the cylinder roll receptacle and the further cylinder roll receptacle directly or by way of a transmission unit.

\* \* \* \* \*